United States Patent [19]

Worth

[11] Patent Number: 4,582,851

[45] Date of Patent: Apr. 15, 1986

[54] ANTI-BACTERIAL 1,4-AMINOALKYLAMINO-9H-THIOXANTHEN-9-ONE DERIVATIVES, COMPOSITIONS, AND METHOD OF USE THEREFOR

[75] Inventor: Donald F. Worth, Ann Arbor, Mich.

[73] Assignee: Warner-Lambert Company, Morris Plains, N.J.

[21] Appl. No.: 689,058

[22] Filed: Jan. 10, 1985

Related U.S. Application Data

[63] Continuation-in-part of Ser. No. 577,461, Feb. 6, 1984, abandoned.

[51] Int. Cl.[4] .................. C07D 335/16; A01N 43/18; A61K 31/38
[52] U.S. Cl. ...................................... 514/437; 549/27
[58] Field of Search ............... 546/202; 548/525, 527; 549/27; 514/212, 324, 333, 422, 437

[56] References Cited

U.S. PATENT DOCUMENTS 2,732,373  1/1956  Steiger .................................. 549/27

OTHER PUBLICATIONS

Archer et al., C.A. vol. 96, 1982, 96:85378j, 96:85379k, p. 573.
Eiden et al., C.A. vol. 81, 1974 81:169500w, p. 545.

Primary Examiner—Henry R. Jiles
Assistant Examiner—J. G. Mullins
Attorney, Agent, or Firm—Ronald A. Daignault

[57]  ABSTRACT 1,4-Aminoalkylamino-9H-thioxanthen-9-ones have antimicrobial activity and activity against leukemic cells. Methods for their preparation, use and pharmaceutical compositions are described.

9 Claims, No Drawings

ANTI-BACTERIAL 1,4-AMINOALKYLAMINO-9H-THIOXANTHEN-9-ONE DERIVATIVES, COMPOSITIONS, AND METHOD OF USE THEREFOR

CROSS-REFERENCE TO RELATED APPLICATION

This application is a continuation-in-part of U.S. Ser. No. 577,461 of Feb. 6, 1984 now abandoned.

BACKGROUND OF THE INVENTION

Experimental antitumor activity has been reported for thioxanthenones notably lucanthone 1a and hycanthone 1b

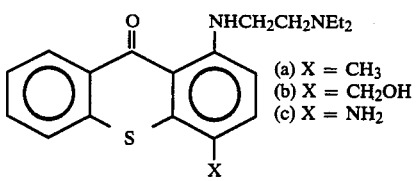

(a) X = CH$_3$
(b) X = CH$_2$OH
(c) X = NH$_2$ and recently the 7-hydroxy analog of lucanthone has been shown to have in vivo P388 activity.

S. Archer, K. J. Miller, R. Rej, C. Periana, and L. Fricker, *J. Med. Chem.*, 25, 220 (1982).

S. Archer, A. H. Zayed, R. Rej, and T. A. Rugino, *J. Med. Chem.*, 26, 1240 (1983).

The 4-nitro analog of lucanthone has been described in an earlier paper on the preparation of schistosomiasis drugs.

S. Archer and C. M. Suter, *J. Am. Chem. Soc.*, 74, 4296 (1952).

In a recent paper, the corresponding amino compound (1c) was prepared and shown to be inactive against the P-388 lymphocytic leukemia.

S. Archer and R. Rej, *J. Med. Chem.*, 25, 328 (1982).

The corresponding N,N-dimethylaminoethyl and N-hydroxyethylaminoethyl analogs of lucanthone were also inactive.

SUMMARY OF THE INVENTION

The present invention relates to pharmaceutical compounds having antibacterial, antifungal, and antitumor activity, which are represented by a compound of the formula

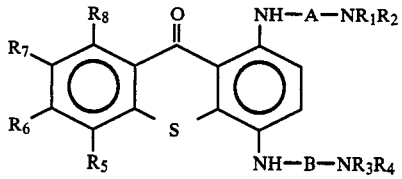

and pharmaceutically acceptable acid addition salts thereof, wherein

R$_5$–R$_8$ each independently represent hydrogen, hydroxy or alkoxy of from 1–4 carbon atoms;

A and B are each independently a straight or branched alkylene chain of from 2–5 carbon atoms, optionally substituted with hydroxyl;

R$_1$, R$_2$, R$_3$, and R$_4$ are H or straight or branched alkyl of 1–4 carbon atoms, optionally substituted with hydroxyl and R$_1$ and R$_2$, or R$_3$ and R$_4$ when taken together represent

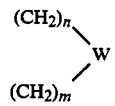

wherein n and m are each an integer from 2–3 and W is a direct bond or O, S or NR$^9$ wherein R$^9$ is H or straight or branched alkyl of from 1–4 carbon atoms, optionally substituted with hydroxyl.

The present invention also includes pharmaceutical compositions for treating bacterial, fungal infections or tumors such as lymphocytic leukemia in warm-blooded animals comprising an effective amount of a compound of formula I in admixture with a pharmaceutically acceptable carrier or diluent.

The present invention further includes a method of treating bacterial or fungal infections as well as tumors such as lymphocytic leukemias in warm-blooded animals which comprise administering to said warm-blooded animal an effective amount of a compound of the formula I in unit dosage form such as a pharmaceutical composition as herein defined.

The present invention also includes novel intermediates of the formula III wherein R$_1$–R$_8$ and A are as defined above. These compounds are also useful pharmacologically as antitumor agents.

The compounds of the invention may be prepared conveniently by the following reaction sequence

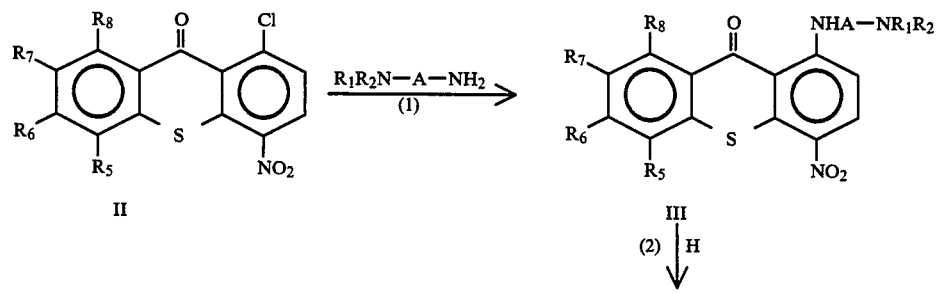

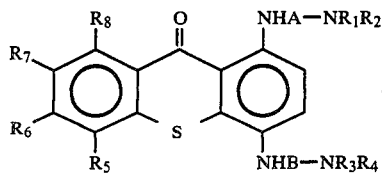 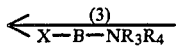 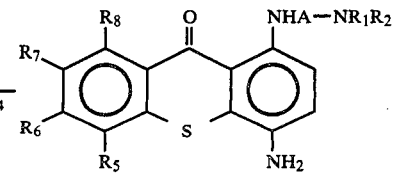

I    IV

The reaction step (1) is carried out as described in S. Archer and C. M. Suter, J. Am. Chem. Soc., 74, 4296 (1952). Reduction of the 4-nitro group of the compound of the formula II is carried out by known methods using catalytic hydrogenation with, for example, hydrogen in the presence of Raney nickel catalyst at elevated temperatures in an inert solvent such as an alcohol, e.g. ethanol, or with 10% palladium on carbon catalysts in a hydrogenator where hydrogen is at a pressure of approximately 40 psi or 1 atmosphere.

The reaction step (3) is carried out in the usual way in an inert solvent at room or elevated temperatures. Here X is halogen, preferably bromine or chlorine, and the reaction may be carried out in the presence of base or other appropriate acid acceptor, such as triethylamine, pyridine, and the like.

When $-NR_1R_2$ is a secondary amine, i.e., $R_1$ or $R_2$ is hydrogen, said amine can be appropriately blocked with an amino protecting group prior to alkylation, step (3). Blocking groups such as t-butyloxycarbonyl or benzyloxycarbonyl can be used which are conveniently removed following the alkylation reaction.

Alternatively when $-NR_3R_4$ is a secondary amine and substituted by hydroxyl, the alkylation may be carried out with a haloalkyleneoxazolidine as, for example, specifically illustrated in Example 1. Ring opening of the oxazolidine moiety affords the desired hydroxyalkylaminoalkylene group attached to the 4-amino position.

The compounds of the invention form pharmaceutically acceptable salts with both organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic, isethionic, lactic, gluconic, glucuronic, sulfamic, benzoic, tartaric, pamoic, and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, with pharmaceutically acceptable solvents such as water, ethanol and the like are equivalent to the unsolvated forms for purposes of the invention.

The term halogen is intended to include fluorine, chlorine, bromine, and iodine.

The alkyl and alkoxy groups contemplated by the invention, unless specified otherwise, comprise both straight and branched carbon chains of from one to about four carbon atoms. Representative of such groups are methyl, ethyl, isopropyl, butyl, sec-butyl, isobutyl, t-butyl, methoxy, ethoxy, i-propoxy, t-butoxy, and the like.

The alkylene groups contemplated by the invention, unless specified otherwise, comprise both straight and branched carbon chains of from two to about 5 carbon atoms. Representative of such groups are ethylene, n-propylene, n-butylene, i-propylene, and the like. The preferred alkylene groups of the invention have the following structural formulas:

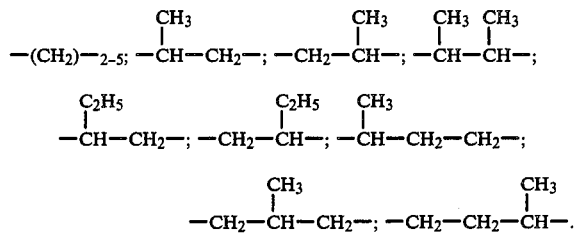

Accordingly, a preferred embodiment of the present invention includes a compound of the formula I wherein $R_5-R_8$ are hydrogen; A, B, $R_1$, $R_2$, $R_3$, and $R_4$ are as defined above, and pharmaceutically acceptable acid addition salts thereof.

Another preferred embodiment of the present invention includes a compound of the formula I wherein $R_5-R_8$ are hydrogen, A and B are each independently ethylene or propylene, $R_1$, $R_2$, $R_3$, and $R_4$ are as defined above and pharmaceutically acceptable acid addition salts thereof.

Still another preferred embodiment of the present invention includes a compound of the formula I wherein $R_5-R_8$ are hydrogen, A and B are each independently ethylene or propylene, $R_1$, $R_2$, $R_3$, and $R_4$ are each independently hydrogen, methyl, ethyl, or hydroxyethyl and pharmaceutically acceptable acid addition salts thereof.

Particular embodiments of the present invention include 1-[[2-(dimethylamino)ethyl]amino]-4-[[2-[(2-hydroxyethyl)amino]-ethyl]amino]-9H-thioxanthen-9-one; 4-[(2-aminoethyl)amino]-1-[[2-dimethylamino]-ethyl]-9H-thioxanthen-9-one, and 4-[(3-aminopropyl)amino]-1-[[2-dimethylamino)ethyl]amino]-9H-thioxanthen-9-one and pharmaceutically acceptable acid addition salts thereof.

The compounds of the invention are new chemical substances of value as pharmacological agents for the treatment of bacterial and fungal infections in warm-blooded animals. The antibacterial and antifungal activity of representative compounds of the invention was established by the screening procedure described below.

In addition to their usefulness as antibacterial and antifungal agents, compounds of the invention display in vitro and in vivo antitumor activity.

1. Preparation of inocula (A) Bacteria and yeast:

The bacterial and yeast isolates are maintained in agar slants or in liquid media, hereby designated as inoculum media. The cultures are transferred at regular intervals in such media. (See Table for the corresponding inoculum media of each culture.) The organisms are generally transferred on to agar slants or liquid inoculum media and incubated overnight (18–20 hours): 37° C. for the bacterial isolates and 28° C. for the fungal cultures.

The microbial cells from the overnight agar slants are then scraped off and suspended in saline solution (0.85% NaCl). The microbial concentrations are adjusted to a light transmittancy of 20–35%, Junior Coleman Spectrophotometer (555M). For the organisms that are maintained in liquid media, an aliquot of the culture suspension is simply diluted with saline to 20–35% light transmittancy.

The above microbial suspension serve as inocula for the assay plates. Thus, 0.16–10 ml (see Table for exact amount) are used to inoculate 100 ml of the molten-agar assay medium.

(B) Mycelial fungi:

The *Penicillium avellaneum* is grown for six days, at 28° C., on an agar medium. This is to allow sporulation of the culture. The organism is then harvested by scraping off the cells from the agar surface (mycelia and spores) and suspending them in saline solution containing 0.05% Tween 80. The suspension is adjusted to a light transmitancy of 20%. One ml of this suspension is used to inoculate 100 ml of the molten-agar assay medium.

2. Preparation of assay plates

Stainless steel frames, 12.3×25.3 cm (ID) and glass plates, 15.3×31.7 cm are used to make the test trays. The frames are attached to the plates with tape at each end and the inner edges sealed with 2% agar. Twenty five ml of inoculated assay medium is spread evenly on each tray and allowed to solidify. The trays are covered, inverted, and refrigerated until used.

3. Disking of samples

The compounds or samples to be tested are dissolved in suitable solvents, e.g., alcohols, dimethylsulfoxide, or N,N-dimethylformamide. The samples are generally dissolved so that the final concentration of the solvent is <10%.* The compounds are tested at different concentrations: 3,000; 1,000; 500; 100; and 10 mcg/ml. Paper discs (12.7 mm diameter) are placed on the agar trays with forceps, then 0.08 ml of the dissolved compound is pipetted onto each disc using a 0.2 ml pipette. (*If the compound does not stay in solution at <10% alcohol, then the full strength alcohol is used. However, the impregnated discs are air-dried before they are laid on to the seeded agar plates.)

4. Interpretation of results

The disked agar trays are incubated overnight (18–20 hours) at 37° C. for the bacterial cultures and 28° C. for the yeasts. The *Penicillium avellaneium* tray is incubated for at least 20–24 hours since it is a slower-growing organism. Active compounds show a zone of inhibition around the disc. The diameter of the zone is measured in mm. The zone diameter of active compounds ranges from a minimum of 13.5 mm to as high as 60 mm. The size of the zone diameter generally reflects the activity of the compound: the larger the zone the greater the activity.

TABLE

| Culture | Number | Inoculum Medium | Inoculum Level ml/100 ml | Assay Medium |
|---|---|---|---|---|
| Aerobacter aerogenes | 0126 | Veal Infusion Broth | 1 | Mycin Agar |
| Escherichia coli | 04863 | AM-08 Agar | 1 | AM-08 |
| Bacillus subtilis | 04555 | AM-08 Broth | 0.5 | AM-08 |
| Streptococcus faecalis | 05045 | Folic Acid Assay Broth | 2 | AM-09 |
| Penicillium avellaneum | M2988 | AM-Agar | 1 | AM-25 |

5. Culture media

The composition of the various culture media, except for the commercially available media, are shown below. The commercial ready-made Veal Infusion Medium is obtained from Difco Laboratories, Detroit, Mich., United States. Add 1.5% agar to these media for use as agar plates.

| AM-08 | % |
|---|---|
| Glucose | 0.2 |
| Sodium Glutamate | 1.04 |
| $KH_2PO_4$ | 0.03 |
| $Na_2HPO_4$ | 0.07 |
| Salts #1[a] | 1 ml |
| Salts #2[b] | 10 ml |
| $H_2O$ (distilled) | |

| [a]Salts #1 | % | [b]Salts #2 | % |
|---|---|---|---|
| $MgSO_4$ | 1.0 | $MnSO_4$ | 1.0 |
| $CaCl_2$ | 5.0 | $ZnSO_4.7H_2O$ | 1.0 |
| NaCl | 5.0 | $FeSO_4.7H_2O$ | 1.0 |
| $CuSO_4.5H_2O$ | 0.01 | $H_2O$ (distilled) | |
| $H_2O$ (distilled) | | | |

| AM-09 | | |
|---|---|---|
| $K_2HPO_4$ | 3.9 | gm |
| Dextrose | 25 | gm |
| Na-citrate .2 $H_2O$ | 34.4 | gm |
| Casein hydrolysate | 6.2 | gm |
| Asparagine | 375 | mg |
| L-tryptophan | 125 | mg |
| Cysteine | 312.5 | mg |
| Glutathione | 3.1 | mg |
| Thiamine HCl | 250 | g |
| Riboflavin | 625 | g |
| Ca pantothenate | 500 | g |
| Nicotinic acid | 500 | g |
| p-aminobenzoic acid | 625 | g |
| Biotin | 12.5 | g |
| Pyridoxine HCl | 2.5 | g |
| Folic Acid | 500 | g |
| NaCl | 12.5 | g |
| $MgSO_4$ | 250 | g |
| $FeSO_4$ | 12.5 | g |
| $MnSO_4.H_2O$ | 125 | g |
| Tween 80 | 62.5 | mg |
| $H_2O$ (distilled) | 1000 | ml |

| AM-25 | % |
|---|---|
| $Na_2HPO_4.H_2O$ | 0.35 |
| $KH_2PO_4$ | 0.05 |
| Yeast Extract (Difco) | 0.5 |
| Dextrose | 1.0 |
| Distilled Water | |

Utilizing the above described procedure, the results in Table 1 were obtained for representative compounds of the invention.

In Vitro Antitumor Activity

A test protocol uses L1210 cells, a murine leukemia cell line, grown in RPMI 1640 supplemented with 5% fetal bovine serum and gentamicin (50 μg/ml). Drug dilutions are prepared in the appropriate solvent and 20 μl of each dilution are added to 24-well Linbro tissue culture plates, followed by the addition of 2.0 ml of cell suspension containing $3 \times 10^4$ cells per ml. Solvent and medium controls are included in each test. After incubation at 37° C. for three days in 5% $CO_2$, the contents of each well are removed and the cells counted in a ZBI Coulter counter. Percent growth are calculated relative to the controls and the levels of drug activity are expressed as $ID_{50}$ in moles per liter.

In addition to their usefulness as antibiotic and antifungal agents and as antileukemic agents, certain of the compounds of the invention display in vitro activity against solid tumors when tested by the following procedure.

HCT-8 (human colon adenocarcinoma) cells are trypsinized using Trypsin-EDTA. A single cell suspension is achieved by passing the cells through a 26 gauge needle with a 20 cc syringe. A cell suspension is prepared using RPMI 1640 growth medium (available from Gibco Laboratories)+10% fetal calf serum+50 μg/ml gentamycin with a cell concentration of approximately 30,000 cells/ml. The cell suspension is dispensed in Linbro 24-well plates; 1 ml/well. The plates are incubated for approximately 48 hrs at 37° C. in a 5% $CO_2$ atmosphere. At this time test compounds are added in the appropriate concentration. Five μl of the 200 μg/ml stock solution is added to each well in a primary test. Ten μl of the appropriate dilution is added to each well for a titration test. The plates are reincubated an additional 60–65 hrs at 37° C. in a 5% $CO_2$ atmosphere. The test is read by lysing the cells using a mix of cationic surfactant, glacial acetic acid and sodium chloride. Two ml of the lysed cell suspension from each well is added to 8 ml of diluent. Each sample is read with a Coulter counter (ZBI model). The activity of each sample is measured as a percentage of the controls and the data is reported as $ID_{50}$, that is the molar quantity of drug required to kill 50% of the tumor cells.

In Vivo Activity

The in vivo lymphocytic leukemia P388 test is carried out by the United States National Cancer Institute. The animals used are either male or female $CD_2F_1$ mice. There are six to seven animals per test group. The tumor transplant is by intraperitoneal injection of dilute ascitic fluid containing cells of lymphocytic leukemia P388. The test compounds are administered intraperitoneally in two single doses with a four-day interval between doses at various dose levels following tumor inoculation. The animals are weighed and survivors are recorded on a regular basis for 30 days. A ratio of survival time for treated (T)/control (C) animals is calculated. The criterion for efficacy is $T/C \times 100 > 125\%$. The positive control compound in this test is 1,4-dihydroxy-5,8-[bis[[2-[(2-hydroxyethyl)amino]-ethyl]-]amino]-9,10-anthracenedione given at dosages ranging from 12.0 to 0.075 mg/kg. See *Cancer Chemotherapy Reports*, Part 3, 3, 1 (1972) for a comprehensive discussion of the protocol.

Utilizing these procedures, the results in Table 1 were obtained for representative compounds of the invention.

TABLE 1

Antitumor, Antibacterial, and Antifungal Data on 1,4-Aminoalkylamino-9H—thioxanthen-9-ones

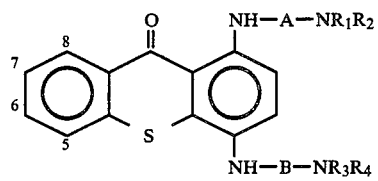

| | | | | | P388 in vivo | | | Inhibitory Zone Diameter (Conc. in mg/ml) | | | |
|---|---|---|---|---|---|---|---|---|---|---|---|
| Example No. | NHA—NR₁R₂ | NHBNR₃R₄ | L1210 in vitro ID₅₀ (M) | HCT-81 in vitro ID₅₀ (M) | Dose (mg/kg) | T/C × 100 | E. coli | B. Subtilis | S. Faeculic | A. Viscolacti | N. Catarrhali |
| 1 | NHCH₂CH₂NMe₂ | NHCH₂CH₂NHCH₂CH₂OH | 6.1 × 10⁻⁷ | — | 25 125 | 236 (1)* 190 | 17 (3000) | 19 (100) | 19 (1600) | 17 (100) | 21 (100) |
| 2 | NHCH₂CH₂NMe₂ | NHCH₂CH₂NH₂ | 6.0 × 10⁻⁷ | 5.9 × 10⁻⁷ | 25 12.5 | 212 (1)* 187 | 14 (1000) | 16 (100) | 14 (500) | 23 (100) | 20 (100) |
| 3 | NHCH₂CH₂NMe₂ | NH(CH₂)₃NH₂ | 2.6 × 10⁻⁶ | — | 25 | 125 | 0 | 16 (1000) | 18 (3000) | 14 (100) | 24 (100) |

*Number of animals surviving 30 days and considered "cured."

TABLE 2

Antitumor, Antibacterial, and Antifungal Data on
1,4-Aminoalkylamino-9H—thioxanthen-9-ones

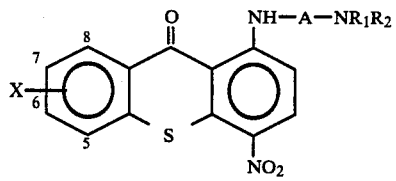

| Example No. | NHA—NR$_1$R$_2$ | X | L1210 in vitro ID$_{50}$ (M) | HCT-8- in vitro ID$_{50}$ (M) | P388 in vivo Dose (mg/kg) | T/C × 100 | Inhibitory Zone Diameter (Conc. in mg/ml) |
|---|---|---|---|---|---|---|---|
| 5 | NH(CH$_2$)$_3$NMe$_2$ | H | 9.6 × 10$^{-8}$ | 4.6 × 10$^{-7}$ | 50 | 190 | |
| 5 | NH(CH$_2$)$_2$NMe$_2$ | 7-OMe | 2.5 × 10$^{-7}$ | 1.0 × 10$^{-6}$ | 100 | 178 | |
| 5 | NH(CH$_2$)$_2$NMe$_2$ | 7-OH | 6.5 × 10$^{-9}$ | — | — | — | |
| 5 | NH(CH$_2$)$_2$NEt$_2$ | 6-OMe | 1.2 × 10$^{-6}$ | 1.1 × 10$^{-6}$ | 100 | 104 | |
| 4 | NH(CH$_2$)$_2$NMe$_2$ | H | 1.2 × 10$^{-7}$ | 2.7 × 10$^{-7}$ | — | — | |
| 5 | NH(CH$_2$)$_2$NEt$_2$ | 7-OH | | | | | |

When being utilized as antibiotic and antifungal agents, the compounds of the invention can be prepared and administered in a wide variety of topical, oral, and parenteral dosage forms. It will be clear to those skilled in the art that the following dosage forms may comprise as the active component, either a compound of formula I, certain of the compounds of formula II or a corresponding pharmaceutically acceptable salt of one of said compounds or a mixture of such compounds and/or salts.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Topical preparations include dusting powders, creams, lotions, gels, and sprays. These various topical preparations may be formulated by well known procedures. See for example Remington's Pharmaceutical Sciences, Chapter 43, 14th ed. 1970, Mack Publishing Co., Easton Pa., 18042, United States.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged form.

The quantity of active compound in a unit dose of preparation may be varied or adjusted from 50 mg to 500 mg according to the particular application and the potency of the active ingredient.

In therapeutic use as antibiotic and antifungal agents the compounds utilized in the pharmaceutical method of this invention are administered at the initial dosage of about 0.1 mg to about 50 mg per kilogram. A dose range of about 0.5 mg to about 10 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing, a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitation inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 500 mg, with from about 0.5 to about 250 mg being preferred. Expressed in proportions, the active compound is generally present in from about 0.1 to about 500 mg/ml of carrier. In the case of compositions containing supplementary active ingredients, the dosages are determined by reference to the usual dose and the manner of administration of the said ingredients. The daily parenteral doses for mammalian subjects to be treated ranges from 0.1 mg/kg to 100 mg/kg. The preferred daily dosage range is 0.3 mg/kg to 10 mg/kg.

The following nonlimiting examples illustrate the inventors' preferred methods for preparing the compounds of the invention.

EXAMPLE 1

1-[[2-(Dimethylamino)ethyl]amino]-4-[[2-[(2-hydroxyethyl)amino]ethyl]amino]-9H-thioxanthen-9-one trihydrochloride A mixture of 1-[(2-(dimethylamino)ethyl)amino]-4-aminothio-xanthenone (5.0 g, 0.016 mole) and 10 g of 3-$\beta$-chloroethyloxazolidinone was flushed with argon for 0.5 hours and heated in an oil bath for eight hours at 100°. The reaction mixture was dissolved in 250 ml of $CH_2Cl_2$ and 250 ml of 2NNaOH. The organic layer was extracted with 250 ml of 2NNaOH. The organic layers were combined, washed with water, dried over $MgSO_4$ and evaporated to dryness in vacuo. The resultant solid was purified by flash chromatography using 410 g of silica gel in a column with an outside diameter of 8.5 cm. Elution with $CH_2Cl_2$:MeOH (11:1) provided 2.2 g of 3-[2-[[1-[[2- dimethyamino)ethyl]amino]-9-oxo-9H-thioxanthen-4-yl]amino]ethyl]-2-oxazolidinone as a red solid. This was dissolved in 20 ml of 2NKOH in MeOH, 10 ml of water and 10 ml of tetrahydrofuran, flushed with argon and heated under reflux overnight. The organic material was removed in vacuo, 40 ml of water was added, and the mixture was extracted with methylene chloride. The extracts were washed with water, dried over $MgSO_4$, and concentrated to dryness. The red solid was purified by flash chromatography using 180 g of silica gel and a 50 mm column. Elution with $CH_2Cl_2$.MeOH.$Et_3N$ (49:49:2) and evaporation provided 14 g of product which was dissolved in 40 ml of EtOH and added to a large volume of 2-propanol saturated with gaseous HCl. The mixture was warmed gently on the steam bath, cooled, and filtered to give 1.6 g of the product as a yellow solid, mp 260° (dec).

Similarly may be prepared:
1-[[3-(Dimethylamino)propyl]amino]-4-[[2-[2(2-hydroxyethyl)amino]ethyl]amino]-9H-thioxanthen-9-one from 1-[[(3-dimethylamino)propyl]amino]-4-aminothioxanthenone.
1-[[3(-Dimethylamino)propyl]amino]-4-[[2-[2(2-hydroxyethyl)amino]ethyl]amino]-7-methoxy-9H-thioxanthen-9-one from 1[[(3-dimethylamino)propyl]amino]-7-methoxy-4-aminothioxanthenone.

1-[[2-(Diethylamino)ethyl]amino]-4-[[2-[(2-hydroxyethyl)amino]ethyl]amino]-6-methoxy-9H-thioxanthen-9-one from 1-[[(2-diethylamino)ethyl]amino]-6-methoxy-4-aminothioxanthenone.

EXAMPLE 2

4-[(2-Aminoethyl)amino]-1-[[2-(dimethylamino)ethyl]amino]-9H-thioxanthen-9-one, hydrochloride A mixture of 4.0 g (0.013 mole) of 1-[[2-dimethylamino)ethyl]-amino]-4-aminothioxanthenone and 8.0 g (0.039 mole) of 2-bromoethylamine hydrobromide in 90 ml of ethanol was heated under reflux for three days. A further 8 g of 2-bromoethylamine hydrobromide and 10 ml of water was added and heating continued for four days. The reaction mixture was concentrated in vacuo and 50 ml of ethanol was added. The solid was collected, washed with ethanol and dried in vacuo at 60° to give 7 g of red solid. This material was dissolved in 200 ml of water, filtered, and 26 ml of 2NNH$_4$OH was added. The mixture was extracted with methylene chloride dried over MgSO$_4$ and concentrated in vacuo to a red oil which solidified (4 g). Purification by flash chromatography over 240 g of silica gel in a 100 mm column and elution with CH$_2$Cl$_2$.MeOH (1:1) to remove starting material and then with CH$_2$Cl$_2$/MeOH/Et$_3$N (49:49:2) provided 2.3 g of the product. The solid was dissolved in 90 ml of ethanol and treated with 2-propanol saturated with gaseous hydrogen chloride to provide 2.5 g of the product, mp 264° (dec).

Similarly may be prepared:
4-[(2Aminoethyl)amino]-1-[[3-(dimethylamino)propyl]amino]-9H-thioxanthen-9-one from 1-[[(3-dimethylamino)propyl]amino]-4-amino-thioxanthenone.
4-[(2-Aminoethyl)amino]-1-[[3-(dimethylamino)propyl]amino]-7-methoxy-9H-thioxanthen-9-one from 1-[[(3-dimethylamino)propyl]amino]-7-methoxy-4-aminothioxanthenone.
4-[(2-Aminoethyl)amino]-1-[[2-(diethylamino)ethyl]amino]-6-methoxy-9H-thioxanthen-9-one from 1-[[(2-diethylamino)ethyl]amino]-6-methoxy-4-aminothioxanthenone.

EXAMPLE 3

4-[(3-Aminopropyl)amino]-1-[[2-(dimethylamino)ethyl]amino]-9H-thioxanthen-9-one, trihydrochloride A mixture of 4.0 g (0.013 mole) of 1-[[2-dimethylamino)ethyl]amino]-4-aminothioxanthenone and 8.5 g (0.039 mole) of 3-bromopropylamine, hydrobromide in 90 ml of ethanol and 10 ml of water was heated under reflux for five days. The mixture was concentrated in vacuo and 50 ml of ethanol was added to the residue. The solid was collected, washed with cold ethanol and dried in vacuo at 10° to give 6.5 g of light orange solid. This material was dissolved in 100 ml of water, treated with 26 ml of 2NNH$_4$OH and extracted with methylene chloride. The extracts were dried over MgSO$_4$ and concentrated in vacuo to give 3.35 g of a dark red solid. Flash chromatography was used (200 g silica gel, 60 mm d. column) to provide (CH$_2$Cl$_2$:MeOH:Et$_3$N) (49:49:2) a dark red solid. The material was dissolved in 90 ml of ethanol and treated with 2-propanol saturated with HCl. Filtration and drying provided 2.8 g of yellow solid. Recrystallization from 200 ml of EtOH-H$_2$O (9:1) gave 1.4 g of a yellow solid, mp 276°-285° (dec).

Nitro compounds of formula III utilized for the preparation of the compounds of formula I are described below.

EXAMPLE 4

1-[[2-(dimethylamino)ethyl]amino]-4-nitro-9H-thioxanthen-9-one

A solution of 9.3 g (0.105 mole) of N,N-dimethylethylenediamine in 35 ml of xylene was added dropwise over ten minutes to a stirred mixture of 1-chloro-4-nitrothioxanthone (24.5 g, 0.084 mole) and K$_2$CO$_3$ (12.2 g, 0.088 mole) in 350 ml of xylene. The mixture was heated for one hour at 70°, an additional 1.8 g (0.088 mole) of N,N-dimethylethylendiamine was added, and heating was continued for an additional hour. The mixture was cooled and the solid was collected, washed with cold xylene, petroleum ether, dried, triturated with water, and dried in vacuo at 70° to give the product (24.7 g) as a yellow solid, mp 177°-179°.

Treatment of a solution of this material in methanol with excess methanesulfonic acid gave the corresponding salt, mp 242°-246°.

EXAMPLE 5

1-[[3-(dimethylamino)propyl]amino]-4-nitro-9H-thioxanthen-9-one

A solution of 8.5 g (2 equiv) of N,N-dimethylpropylenediamine in 50 ml of N,N-dimethylformamide was added in one portion to a suspension of 10 g (0.037 mole) of 1-chloro-4-nitrothioxanthone in 100 ml of N,N-dimethylformamide. The mixture was stirred at room temperature for five hours and then heated on a steam bath for 0.5 hour. The mixture was allowed to cool to room temperature and 100 ml of 2-propanol was added. Cooling at 0° for two hours gave a solid which was collected, washed successively with 2-propanol, water and 2-propanol, and dried in vacuo at 60° for 16 hours to afford 10.2 g of the product as a yellow solid, mp 105°-108°.

1-[[2-(Dimethylamino)ethyl]amino]-7-methoxy-4-nitro-9H-thioxanthen-9-one was prepared similarly from 8.0 g of 1-chloro-7-methoxy-4-nitrothioxanthone and 5.6 g of N,N-dimethylethylenediamine affording 7.2 g, mp 190°-192°.

1-[[2-(Dimethylamino)ethyl]amino]-6-methoxy-4-nitro-9H-thioxanthen-9-one was prepared similarly from 0.99 g of 1-chloro-6-methoxy-4-nitrothioxanthone and 0.67 g of N,N-diethylethylenediamine affording 0.98 g, mp 144°-145°.

1-[[2-(Dimethylamino)ethyl]amino]-7-hydroxy-4-nitro-9H-thioxanthen-9-one was prepared similarly from 10 g of 1-chloro-7-hydroxy-4-nitrothioxanthone and 5.7 g of N,N-dimethylethylenediamine to provide 7.2 g, mp>300°.

1-[[2-(Diethylamino)ethyl]amino]-7-hydroxy-4-nitro-9H-thioxanthen-9-one was prepared similarly from 10 g of 1-chloro-7-hydroxy-4-nitrothioxanthone and 8.3 g of N,N-diethylethylenediamine to provide 7.3 g as a tan solid which was used without further purification.

The requisite 1-chloro-7-methoxy-4-nitrothioxanthone was prepared as follows: A mixture of 118.5 g (0.35 mole) of 2-(5-chloro-2-nitrophenylthio)-5-methoxybenzoic acid and 131 ml of thionyl chloride in 600 ml of toluene was heated under reflux for 1.5 hours. The mixture was concentrated in vacuo, and the resulting solid was dissolved in 950 ml of nitrobenzene with heating and then cooled to 0° in an ice bath. Aluminum chloride (44.2 g) was added in portions over 0.5 hour with cooling, and the mixture was then allowed to come to room temperature and stirred overnight. The mixture was poured into 5 l of cold water. As much of the water layer as possible was decanted. The residue was triturated twice with 1 l portions of methanol and then twice with 2 l portions of methanol. The oil was triturated with 4 l of methanol and a solid resulted. This was washed with methanol and dried in vacuo at 75° to give 72.7 g of the product as a brownish-yellow solid, mp 235°–240°.

The requisite 2-(5-chloro-2-nitrophenylthio)-5-methoxybenzoic acid was prepared as follows. A solution of 93.5 g (0.56 mole) of 2-amino-5-methoxybenzoic acid and 38.6 g (0.56 mole) of sodium nitrite in 700 ml of water containing 44 ml of 50% aqueous sodium hydroxide (1.05 mole) was purged with nitrogen and added, under nitrogen, dropwise to a stirred mixture of 175 ml of concentrated hydrochloric acid and 230 g of ice cooled in an ice-salt bath to −10°. The mixture was allowed to stir at 0° for one hour, neutralized to pH 5.1 with potassium acetate, and transferred to an addition funnel using nitrogen pressure. The addition funnel was attached to a 5 l flask containing a solution of potassium ethyl xanthate (259 g, 1.6 mole) in 940 ml of water heated to 80°, and the diazonium salt was added in a thin stream over one hour, maintaining the temperature at 75°–80°. To the hot reaction mixture was added 97.5 g (0.56 mole) of sodium dithionite, and the mixture was then allowed to cool to 20° and acidified to pH 2.4 under nitrogen with concentrated hydrochloric acid (200 ml). Methylene chloride (1.2 l) was added, the mixture was stirred vigorously and the insoluble material removed by filtration. Maintaining the solutions under nitrogen as much as possible, the methylene chloride layer was separated and the aqueous layer was extracted again with methylene chloride (1.2 l). The combined extracts were dried over MgSO$_4$, concentrated in vacuo at 50°, and the crude thiol was warmed with 470 ml of ethanol and added under nitrogen to a solution of 107.5 g of 2,4-dichloronitrobenzene in sodium ethoxide (prepared from 25.8 g of sodium and 1.1 l of ethanol). The mixture was heated under reflux under nitrogen for one hour, cooled, and the solvent was removed in vacuo. The residue was taken up in 1 l of water and 1 l of ether. The ether layer was removed, and the aqueous layer washed two more times with 1 l portions of ether. The aqueous layer was acidified with concentrated hydrochloric acid (50 ml), and the solid was collected, washed with water and dried in vacuo. The solid (99.2 g) was recrystallized from 2.3 l of toluene to give 53.8 g of product, mp 178°–183°, which was sufficiently pure for use in the next step.

The requisite 1-chloro-6-methoxy-4-nitrothioxanthone was prepared as follows: To a prewashed (pentane) suspension of NaH in 500 ml of tetrahydrofuran cooled to 0° was added dropwise over about 25 minutes a solution of 35.4 g of 2,6dichloro-5-nitrobenzoic acid in 200 ml of tetrahydrofuran. After about five minutes a solution of 20 g of m-methoxybenzenethiol in 50 ml of tetrahydrofuran was added, and the mixture was stirred for 20 hours as it gradually came to ambient temperature. The mixture was treated with a 10% aqueous hydrochloric acid solution, extracted into ethyl acetate, dried, and the solvent was removed in vacuo. The orange gum was purified by flash chromatography on SiO$_2$ with a 90:5:0.5 mixture of methylene chloride:methanol:acetic acid. The resulting oil was sufficiently pure for use in the next step. A solution of this material (24.8 g) in 120 ml of trifluoroacetic acid was treated with 60 ml of trifluoroacetic anhydride and allowed to stir at room temperature for 30 minutes. The solution was diluted with acetonitrile, and the precipitate was collected and triturated with boiling acetonitrile to give 15.8 g of the product, mp 254°–258°.

The requisite 1-chloro-7-hydroxy-4-nitrothioxanthone was prepared as follows: To a suspension of 5.0 g of 1-chloro-7-methoxy-4-nitro-thioxanthone in 50 ml of methylene chloride was added 20 ml of boron tribromide in methylene chloride (1M). The mixture was stirred for two days, and an additional 20 ml of boron tribromide was added. The mixture was stirred for three hours at room temperature and heated under reflux for two hours. An additional 20 ml of boron tribromide was added and the mix was heated under reflux for two hours. The mixture was cooled in an ice bath and 50 ml of methanol was added carefully. The solution was heated under reflux for one hour, and the solvent was removed in vacuo. The residue was boiled in about 50 ml of ethanol, collected, and retreated with hot ethanol to provide the product as an orange powder, mp 240°–254° (dec).

I claim:
1. A compound of the formula

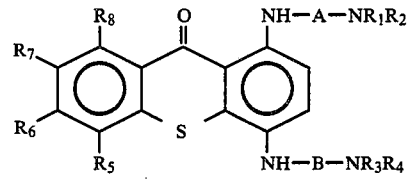

and pharmaceutically acceptable acid addition salts thereof, wherein $R_5$–$R_8$ are each independently hydrogen, hydroxy, or alkoxy of from 1–4 carbon atoms; A and B are each independently a straight or branched alkylene chain of from 2–5 carbon atoms which are unsubstituted or substituted by hydroxyl and $R_1$–$R_4$ are each independently hydrogen or a straight or branched alkyl of 1–4 carbon atoms which are unsubstituted or substituted by hydroxy.

2. A compound according to claim 1, wherein $R_5$–$R_8$ are hydrogen.

3. A compound according to claim 2 wherein A and B are each independently ethylene or propylene.

4. A compound according to claim 3, wherein $R_1$–$R_4$ are each independently hydrogen, methyl, ethyl, or hydroxyethyl.

5. A compound according to claim 4, and being 1-[[(2-(dimethylamino)ethyl]amino]-4-[[2-[(2-hydroxyethyl)amino]-ethyl]-amino]-9H-thioxanthen-9-one.

6. A compound according to claim 4, and being 4-[(2-aminoethyl)amino]-1-[[2-(dimethylamino)ethyl]amino]-9H-thioxanthen-9-one.

7. A compound according to claim 4, and being 4-[(3-aminopropyl)amino]-[[2-(dimethylamino)ethyl]amino]-9H-thioxanthen-9-one.

8. An antibacterial composition comprising an antibacterially effective amount of a compound according to claim 1 in combination with a pharmaceutically acceptable carrier.

9. A method for treating bacterial infections in a mammal which comprises administering to said mammal in need thereof a composition according to claim 8.

* * * * *